United States Patent [19]

Hillegass et al.

[11] Patent Number: 4,817,637
[45] Date of Patent: Apr. 4, 1989

[54] SUBCUTANEOUS INJECTION AND WITHDRAWAL SITE

[75] Inventors: Donald V. Hillegass, Franksville; Eric J. Woodruff, Racine, both of Wis.

[73] Assignee: Medical Engineering Corporation, Racine, Wis.

[21] Appl. No.: 125,431

[22] Filed: Nov. 25, 1987

[51] Int. Cl.⁴ ............................................. A61B 19/00
[52] U.S. Cl. ..................................... 128/899; 604/244
[58] Field of Search ................... 604/244, 264, 87, 93, 604/148, 175, 200; 128/1 R, 899; 623/8

[56] References Cited

U.S. PATENT DOCUMENTS

| | | | |
|---|---|---|---|
| 4,217,889 | 8/1980 | Radovan et al. | 623/8 |
| 4,643,733 | 2/1987 | Becker | 623/8 |
| 4,651,717 | 3/1987 | Jakubczak | 623/7 |
| 4,710,174 | 12/1987 | Moden et al. | 604/244 |

Primary Examiner—Stephen C. Pellegrino
Attorney, Agent, or Firm—Stuart E. Krieger

[57] ABSTRACT

An implantable fluid transfer device or septum which includes a hollow spherical housing containing a chamber therein for receiving fluid. A needle infuses fluid into or withdraws fluid from the chamber. The housing has a surface that is capable of both omni-directional penetration by the needle and sealing itself when the needle is withdrawn from the housing. A spherical needle stop is provided with the housing to prevent the needle that accesses the chamber from one side of the housing from passing through the opposite side of the housing.

21 Claims, 2 Drawing Sheets

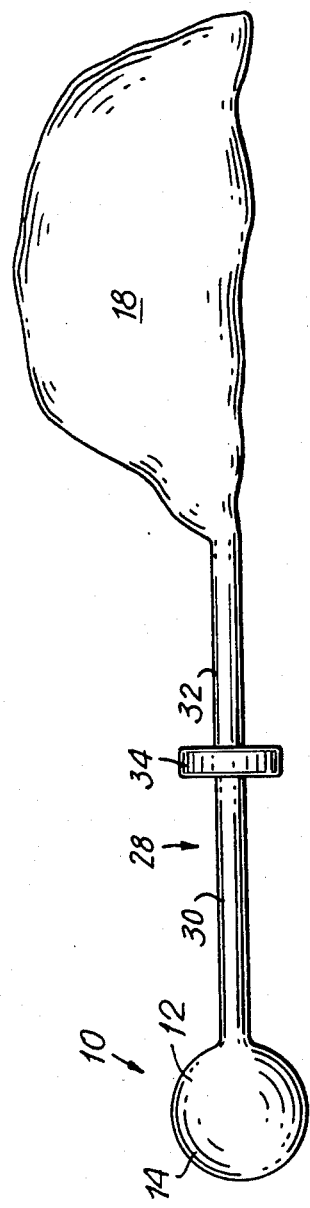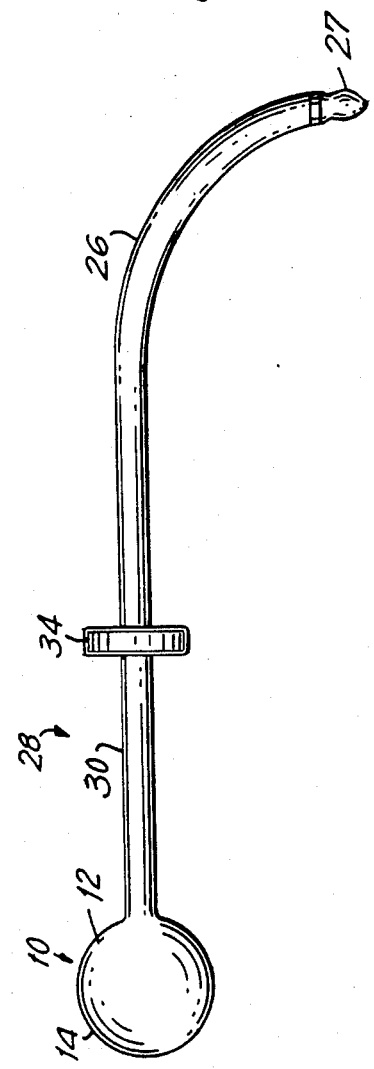

SUBCUTANEOUS INJECTION AND WITHDRAWAL SITE

FIELD OF THE INVENTION

The present invention relates to an implantable fluid transfer device and more particularly to a subcutaneous injection and withdrawal site or septum that permits omni-directional access by a needle to an internal chamber for infusion or withdrawal of fluid.

BACKGROUND OF THE INVENTION

Prosthetic devices, generally known as tissue expanders, are implanted in the body to restore shapes and contours that have been surgically altered or accidentally deformed. These devices usually require periodic infusion or withdrawal of fluid to maintain or achieve the desired shape of the prosthesis or to vary the volume of fluid within the prosthesis for the purpose of establishing proper tension to the prosthesis.

Rather than inject the fluid directly into a prosthesis it has been found beneficial to infuse the fluid into a fluid transfer device, occasionally referred to as a septum, which directs the fluid into the prosthesis. These transfer devices or septums, which facilitate the administration of fluid to an interconnected prosthesis are usually implanted below the skin in the vicinity of the prosthesis. Each device is typically connected to the prosthesis by a fill tube.

One type of subcutaneously implanted septum includes a chamber with a dome shaped elastomeric cover and a rigid flat base. The cover provides a needle-penetrable member to infuse liquid into the chamber. A needle is directed through the patient's skin where it accesses the chamber through the cover. When the needle is withdrawn, the cover self-seals so as to prevent fluid leakage from the chamber. The rigid base acts as a needle stop so as to prevent the needle from penetrating entirely through the device and into the patient's body. It is highly desirable to have a septum with a chamber that is easy to access without fear of having the needle passing through the device.

Occasionally, a septum will twist or even flip over after implantation in a patient. This happens especially in obese patients where the skin and tissue that surround the septum are somewhat soft and loose. The twisting occurs when torque is applied to the septum that exceeds the skin and tissue forces which hold the septum in its desired orientation. Known ways of reducing the undesirable movement of the septum include widening the flat base and suturing the septum in place.

Once a septum has twisted, the fill chamber is no longer easily accessible by a needle since the dome is no longer easy to locate and penetrate. Furthermore, twisting of a septum connected to a prosthesis can kink the fill tube preventing fluid from being infused into or withdrawn from the prosthesis.

It is an object of the present invention to provide a septum that is easily accessible for fluid infusion and for fluid withdrawal even when the septum has twisted within the patient.

It is a further object of the present invention to provide a septum that has a substantial needle-penetrable surface area for its size so as to facilitate ease of needle accessibility to the fluid chamber.

It is also an object to reduce the possibility of needle penetrating through the septum into the patient's body while facilitating ease of needle accessibility to the fluid chamber.

It is also considered desirable to accomplish these objectives while reducing the possibility of kinking the fill tube connecting the septum to the prosthesis.

SUMMARY OF THE INVENTION

In accordance with these and other objects there is provided by the present invention an implantable fluid transfer device or septum that is adapted for attachment to an inflatable prosthesis. This device includes a hollow spherical housing containing a chamber therein for receiving fluid. The housing has a surface which is capable of penetration by a needle and which seals itself when the needle is withdrawn from the housing. Fluid is added to or removed from the chamber through the needle. A needle stop is provided within the housing which prevents the needle that accesses the chamber from penetrating through the opposite side of the housing and into the patient's body where it may cause pain or internal damage.

Preferably, the needle stop is spherical in shape and slightly smaller than the housing so as to define a space between the housing and needle stop. It is within this space that the fluid is injected into or withdrawn from the chamber by the needle. The needle stop may be moved by the needle accessing the chamber so as to widen the space proximate to the needle tip.

It is contemplated that fluid will be retained within the chamber and that the needle stop will float within the housing. This floatation will facilitate movement of the needle stop by the tip of the needle.

The septum is connected to the inflatable prosthesis through a fluid flow means, preferably composed of tubing, that permits fluid to flow from the septum to the prosthesis during infusion, and from the prosthesis to the septum during withdrawal. The fluid flow means includes a connector that permits the septum to rotate relative to the prosthesis. An example of this arrangement is a flow mechanism that includes a length of tubing composed of two segments; a conduit extending from the septum and a fill tube from the prosthesis. The fill tube and conduit are connected by a connector that permits rotation of septum and conduit relative to the fill tube and prosthesis. Alternatively, the connector may be placed at the junction of the conduit and the septum. The connector allows the septum to rotate relative to the conduit and prosthesis. The ability of the septum to rotate cuts down on the possibility of kinking the tubing.

The housing includes a portal through which the fluid outlets to the prosthesis and through which the fluid inlets the housing when withdrawn from the prosthesis. The housing may include an offset means composed of a circular array of projections extending from the inner housing wall about the portal so as to prevent the needle stop from blocking and sealing the portal. The projections keep the needle stop offset from the portal thereby permitting fluid to flow through the portal unimpeded by the needle-stop.

DESCRIPTION OF THE DRAWING

Other objects and advantages will become apparent to those skilled in the art when the following detailed description is read in conjunction with the accompanying drawings, wherein:

FIG. 5 is a plan view of the septum of FIG. 1 attached to a tissue expander; and FIG. 6 is a plan view of the septum of FIG. 1 attached to a catheter for introducing fluids into a recipient's body.

DESCRIPTION OF THE PREFERRED EMBODIMENT

Figure 1:
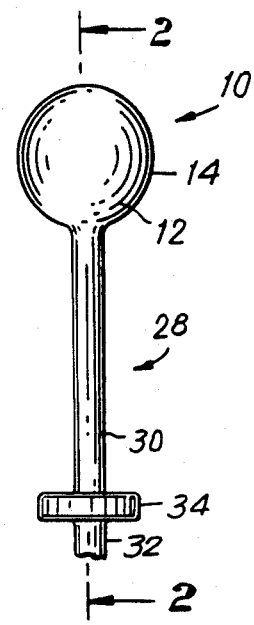
FIG. 1 is a plan view of a septum in accordance with the present invention.
Figure 2:
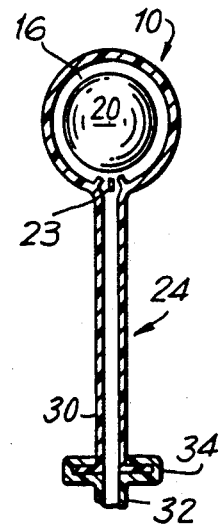
FIG. 2 is a cross-sectional view along line 2—2 of FIG. 1.

Referring now to the drawings wherein a fluid transfer device or septum is generally designated by the numeral 10. This septum includes a housing 12 composed of an elastomeric material that is biocompatible with the human body. An acceptable and preferable material is a silicone elastomer. The housing 12 includes a spherical surface 14 that is capable of being penetrated by a needle 15 and sealing itself when the needle 15 is withdrawn.

Figure 3:
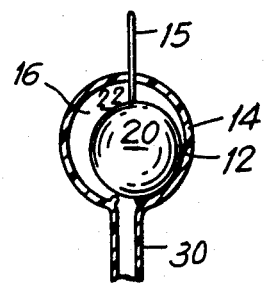
FIG. 3 is a cross-sectional view of a needle accessing the septum of FIG. 1.

The housing 12 defines an inner chamber 16 for receiving fluid which is to be introduced or withdrawn from the chamber 16 through the needle 15 (FIG. 3). The area of the spherical surface 14 and the volume of the chamber 16 can be chosen according to the contemplated use of the septum 10. The spherical shape of the surface 14 provides a substantial target area for the needle to access the inner chamber 16. The septum 10 shown in FIG. 5 is interconnected to an inflatable prosthesis or tissue expander 18. The septum 10 will permit infusion of a fluid into or withdrawal of a fluid from the prosthesis 18 so as to achieve the desired fluid volume.

The housing 12 contains a needle stop member 20 which is impenetrable by a needle 15. The needle stop member 20 may be composed of such material as polycarbonate, polyethylene or the like. This needle stop member 20 is slightly smaller in size and spherical so as to be congruently shaped with respect to the housing 12. Shapes other then spherical will work as a needle stop but do not function as effectively in preventing the needle 15 accessing the chamber 16 from passing through the other side of the housing 12 and into the patient's body. The needle stop member 20 helps to insure that the fluid added or withdrawn occurs within the chamber 16 of the device. The needle stop member 20 is shown as a solid but may be hollow and still properly accomplish its function.

The housing 12 and needle stop member 20 define a space 22 therebetween. This space 22 is the site where the fluid is added or removed from the chamber 16.

The needle stop 20 is constructed of a material that permits it to float within the chamber 16 when the chamber 16 contains a fluid. Accordingly, the needle stop 20 should be the same specific gravity or close to the specific gravity of the injected fluid to allow buoyancy behavior by the needle stop 20. Saline or a silicone based gel are typically used to inflate tissue expanders.

Floating within the chamber 16 permits the spherical needle stop member 20 to be moved or easily repositioned by the needle 15 accessing the chamber 16 so as to increase or widen the space 22 in the vicinity of the needle 15 tip. This space 22, when widened, facilitates the addition or removal of fluid from the chamber 16.

The housing 12 includes a portal 23 through which the fluid outlets to the prosthesis 18 and through which the fluid inlets the housing 12 when withdrawn from the prosthesis 18. The housing 12 includes an offset means composed of a circular array of projections 24 extending from the inner housing wall 25 about the portal 23 so as to prevent the needle stop member 20 from blocking and sealing the portal 23. The projections 24 keep the needle stop member 20 offset from the portal 23 thereby permitting fluid to flow through the portal 23 unimpeded by the needle-stop member 20.

The septum 10 shown in FIG. 5 communicates with an inflatable prosthesis 18. In FIG. 6 the septum 10 is attached to a catheter 26 having a conical dispensing tip 27. The septum 10 and catheter 26 act as a medication infusion system with the fluid chamber 16 communicating through the catheter tip 27 into a blood vessel or organ of the human body instead of a prosthesis.

Figure 4:
FIG. 4 is a plan view of the second embodiment of a septum in accordance with the present invention.

The chamber 16 is interconnected by a fluid flow means generally designated by the numeral 28 to an inflatable prosthesis or tissue expander 18. The flow means includes an access tube or conduit 30 and a fill tube 32. The conduit 30 shown is integrally molded with the spherical housing 12. The conduit 30 is connected to the fill tube 32 by a connecting means. The connecting means is a connector 34 that permits flow therethrough but permits the housing 12 to rotate relative to the fill tube 32 and to the prosthesis 18. Consequently, the septum 10 which provides a spherical surface 14 as an injection site may turn or rotate within the patient's body without cutting down on the surface area targeted by the needle 15 for injection. FIG. 4 shows a septum 10 having a spherical housing 12 that is elliptical instead of circular.

We claim:

1. A septum comprising an implantable hollow spherical housing, said housing being needle-penetrable and self-sealing throughout its surface, said housing defining a chamber therein for receiving fluid, fluid flow means interconnected to said chamber for permitting passage of fluid therethrough, said flow means including a conduit in fluid communication with said chamber, and connector means for permitting rotation of said housing relative to said conduit, and needle stop means within said housing for preventing a needle accessing said chamber from passing through the opposite side of said housing.

2. The septum of claim 1 wherein said fluid flow means interconnects said chamber with an inflatable prosthesis for permitting fluid communication therebetween.

3. The septum of claim 1 wherein said fluid flow means interconnects said chamber with a body part for permitting introduction of fluid into said body part.

4. The septum of claim 1, wherein said flow means includes a conduit secured to said chamber, said conduit having an outlet adapted for infusing fluid into a body part.

5. A septum comprising an implantable hollow spherical housing, said housing being needle-penetrable and self-sealing throughout its surface, said housing defining a chamber therein for receiving fluid, fluid flow means interconnected to said chamber for permitting passage of fluid therethrough, and needle stop means within said housing for preventing a needle accessing said chamber from passing through the opposite side of said housing, said needle stop means including a spherically shaped needle impenetrable member that is slightly smaller and congruently shaped with respect to said housing, said needle impenetrable member and housing defining a fluid receiving space therebetween for receiving fluid from the needle.

6. The septum of claim 5 wherein said fluid flow means includes tubing and connector means incorporated into said tubing for permitting rotation of said housing relative to said prosthesis.

7. The septum of claim 6 wherein said tubing includes a conduit secured to and extending from said chamber and a fill tube secured to and extending from said prosthesis, connector means interconnecting said conduit an said fill tube for permitting fluid flow therebetween and for permitting rotation of said housing relative to said prosthesis.

8. The septum of claim 5, wherein said fluid flow means interconnects said chamber with an inflatable prosthesis for permitting fluid communication therebetween.

9. The septum of claim 5 wherein said fluid flow means interconnects said chamber with a body part for permitting introduction of fluid into said body part.

10. The septum of claim 5, wherein said flow means includes a conduit secured to said chamber, said conduit having an outlet adapted for infusing fluid into a body part.

11. A septum comprising
an implantable hollow spherical housing, said housing being needle-penetrable and self-sealing throughout its surface, said housing defining a chamber therein for receiving and retaining fluid,
fluid flow means interconnected to said chamber for permitting passage of fluid therethrough, and
needle stop means floating within said housing for preventing a needle accessing said chamber from passing through the opposite side of said housing.

12. The septum of claim 11, wherein said fluid flow means interconnects said chamber with an inflatable prosthesis for permitting fluid communication therebetween.

13. The septum of claim 11, wherein said fluid flow means interconnects said chamber with a body part for permitting introduction of fluid into said body part.

14. The septum of claim 11, wherein said fluid flow means includes tubing and connector means incorporated into said tubing for permitting rotation of said housing relative to said prosthesis.

15. The septum of claim 11, wherein said flow means includes a conduit secured to said chamber, said conduit having an outlet adapted for infusing fluid into a body part.

16. A septum comprising
an implantable hollow spherical housing, said housing being needle-penetrable and self-sealing throughout its surface, said housing defining a chamber therein for receiving fluid,
fluid flow means interconnected to said chamber for permitting passage of fluid therethrough, said fluid flow means including a portal in said housing,
needle stop means within said housing for preventing a needle accessing said chamber from passing through the opposite side of said housing, said housing including offset means therein for offsetting said needle stop means from said portal.

17. The septum of claim 16, wherein said fluid flow means interconnects said chamber with an inflatable prosthesis for permitting fluid communication therebetween.

18. The septum of claim 16, wherein said fluid flow means interconnects said chamber with a body part for permitting introduction of fluid into said body part.

19. The septum of claim 16, wherein said fluid flow means includes tubing and connector means incorporated into said tubing for permitting rotation of said housing relative to said prosthesis.

20. The septum of claim 16, wherein said flow means includes a conduit secured to said chamber, said conduit having an outlet adapted for infusing fluid into a body part.

21. The septum of claim 16 wherein said needle stop means includes a needle stop member that is congruently shaped with respect to said housing, said needle stop member and said housing defining a fluid receiving space therebetween for receiving fluid from the needle.

* * * * *